United States Patent [19]
Valiante et al.

[11] Patent Number: 5,688,690
[45] Date of Patent: Nov. 18, 1997

[54] HUMAN CYTOTOXIC LYMPHOCYTE SIGNAL TRANSDUCTION SURFACE PROTEIN (P38) AND MONOCLONAL ANTIBODIES THERETO

[75] Inventors: Nicholas M. Valiante, Palo Alto, Calif.; Giorgio Trinchieri, Wynnewood, Pa.

[73] Assignee: The Wistar Institute of Anatomy and Biology, Philadelphia, Pa.

[21] Appl. No.: 307,280

[22] Filed: Sep. 16, 1994

[51] Int. Cl.$^6$ .......................... C07K 16/00; C07K 16/28; C12N 5/12

[52] U.S. Cl. ................ 435/334; 530/388.1; 530/388.75; 435/343; 435/343.2

[58] Field of Search .......................... 530/350, 387.1, 530/388.1, 388.75; 435/240.27

[56] References Cited

U.S. PATENT DOCUMENTS

| | | |
|---|---|---|
| 4,895,796 | 1/1990 | Lanier et al. |
| 5,124,251 | 6/1992 | Lanier et al. |
| 5,194,593 | 3/1993 | Evans et al. |
| 5,229,494 | 7/1993 | Evans et al. |

FOREIGN PATENT DOCUMENTS

| | | |
|---|---|---|
| 421380 | 4/1991 | European Pat. Off. |
| 528663 | 2/1993 | European Pat. Off. |
| 609901 | 8/1994 | European Pat. Off. |
| WO93/05394 | 3/1993 | WIPO |
| WO93/08835 | 5/1993 | WIPO |

OTHER PUBLICATIONS

A. O'Garra et al., "Role of Cytokines in Determining T–Lymphocyte Function", in *Current Opinion in Immunol.*, 6(3):458–466 (Jun. 1994).

E. Maggi et al., "Ability of HIV to Promote a Th1 to Th0 shift and to Replicate Preferentially in Th2 and Th0 Cells", *Science*, 265:244–252 (Jul. 8, 1994).

N. Valiante and G. Trinchieri, "Identification of a Novel Signal Transduction Surface Molecule on Human Cytotoxic Lymphocytes", *J. Exp. Med.*, 178:1397–1406 (Sep. 17, 1993).

M. Azuma et al., "CD28–T Lymphocytes, Antigenic and Functional Properties", *J. Immunol.*, 150(4):1147–1159 (Feb. 15, 1993).

R. Zinkernagel et al., "Immunological Surveillance Against Altered Self Components by Sensitised T Lymphocytes in Lymphocytic Choriomeningitis", *Nature (London)*, 251:547 (Oct. 11, 1974).

G. Le Gros et al., "Non–Cytotoxic, IL–4, IL–5, IL–10 Producing CD8+ T Cells: Their Activation and Effector Functions", in *Current Opinion in Immunol.*, S. Swain and M. Reth, eds., 6(3):453–457 (Jun. 1994).

L. Lanier et al., "Natural Killer Cells: Definition of a Cell Type Rather than a Function", *J. Immunol.*, 137(9):2735–2739 (Nov. 1, 1986).

G. Trinchieri et al., "Biology of Natural Killer Cells", *Adv. Immunol.*, 47:187–375 (Oct. 1989).

B. Perussia et al., "The Fc Receptor for IgG on Human Natural Killer Cells: Phenotypic, Functional, and Comparative Studies with Monoclonal Antibodies", *J. Immunol.*, 133(1):180–189 (Jul. 1984).

R. Siliciano et al., "Activation of Cytolytic T Lymphocyte and Natural Killer Cell Function Through the T11 Sheep Erythrocyte Binding Protein", *Nature (London)*, 317:428–431 (Oct. 1985).

C. Anasetti et al., "Induction of Calcium Flux and Enhancement of Cytolytic Activity in Natural Killer Cells by Cross–Linking of the Sheep erythrocyte Binding Protein (CD2) and the Fc–Receptor (CD16)", *J. Immunol.*, 139:1772–1779 (Sep. 15, 1987).

W. Hahn et al., "Overlapping but Nonidentical Binding Sites on CD2 for CD58 and a Second Ligand CD59", *Science*, 256:1805–1807 (Jun. 26, 1992).

L. Lanier et al., "Functional and Biochemical Analysis of CD16 Antigen on Natural Killer Cells and Granulocytes", *J. Immunol.*, 141(10):3478–3485 (Nov. 15, 1988).

W. Chambers et al., "Monoclonal Antibody to a Triggering Structure Expressed on Rat Natural Killer Cells and Adherent Lymphokine–Activated Killer Cells", *J. Exp. Med.*, 169:1373–1389 (Apr. 1989).

R. Giorda et al., "NKR–P1, a Signal Transduction Molecule on Natural Killer Cells", *Science*, 249:1298–1300 (Sep. 1990).

F. Karlhofer et al., "Stimulation of Murine Natural Killer (NK) Cells by a Monoclonal Antibody Specific for the NK1.1 Antigen", *J. Immunol.*, 146(10):3662–3673 (May 15, 1991).

J. Ryan et al., "Molecular Cloning of the NK1.1 Antigen, a Member of the NKR–P1 Family of Natural Killer Cell Activation Molecules", *J. Immunol.*, 149(5):1631–1635 (Sep. 1, 1992).

J. Houchins et al., "DNA Sequence Analysis of NKG2, a Family of Related cDNA Clones Encoding Type II Integral Membrane Proteins on Human Natural Killer Cells", *J. Exp. Med.*, 173:1017–1020 (Apr. 1991).

J. Frey et al., "Mechanism of Target Cell Recognition by Natural Killer Cells: Characterization of a Novel Triggering Molecule Restricted to CD3–Large Granular Lymphocytes", *J. Exp. Med.*, 174:1527–1536 (Dec. 1991).

(List continued on next page.)

*Primary Examiner*—Frank C. Eisenschenk
*Attorney, Agent, or Firm*—Howson and Howson

[57] ABSTRACT

The present invention provides a novel monoclonal antibody, mAb C1.7, and its antigenic receptor, p38, which is an NK cell and CD8$^+$ T cell activating structure. Methods of using these compositions to identify and monitor the course of a disease, as well as for therapeutic purposes, are disclosed.

3 Claims, 2 Drawing Sheets

OTHER PUBLICATIONS

D. Evans et al, "Identification of a Putative Antigen Receptor on Fish Nonspecific Cytotoxic Cells with Monoclonal Antibodies", *J. Immunol.*, 141(1):324–332 (Jul. 1, 1988).

D. Harris et al, "Identification of an Evolutionarily Conserved, Function–Associated Molecule on Human Natural Killer Cells", *Proc. Natl. Acad. Sci. USA*, 88:3009–3013 (Apr. 1991).

D. Evans et al, "Identification of a Vimetin–Like Function Associated Molecule (FAM) on Rat NK Cells: Evidence for Receptor Function", *Scand. J. Immunol.*, 37:131–142 (Feb. 1993).

A. Moretta et al, "Novel Surface Molecules Involved in Human NK Cell Activation and Triggering of the Lytic Machinery", *Int. J. Cancer*, 7:6–10 (Nov. 1992).

M. Cassatella et al, "FcyR (CD16) Interaction with Ligand Induces Ca2+ Mobilization and Phosphoinositide Turnover in Human Natural Killer Cells", *J. Exp. Med.*, 169:549–567 (Feb. 1989).

I. Anegon et al, "Interaction of Fc Receptor (CD16) Ligands Induces Transcription of Interleukin 2 Receptor (CD25) and Lymphokine Genes and Expression of Their Human Products in Human Natural Killer Cells", *J. Exp. Med.*, 167:452–472 (Feb. 1988).

M. Smyth et al, "Il–8 Gene Expression and Production in Human Peripheral Blood Lymphocyte Subsets", *J. Immunol.*, 146(1):3815–3823 (Jun. 1, 1991).

C. Morimoto et al, "A Novel Epitope of the LFA–1 Antigen which can Distinguish Killer Effector and Suppressor Cells in Human CD8 Cells", *Nature (London)*, 330 (6147):479–482 (Dec. 3, 1987).

N. Valiante and G. Trinchieri, "Identification of a Novel Signal Transduction Surface Molecule on Human Cytotoxic Lymphocytes", *Tissue Antigens*, 42(4):404 (1993).

Sambrook et al, *Molecular Cloning. A Laboratory Manual*, 2d ed., Cold Spring Harbor Publisher, New York, pp. 2.43–2.84 (Nov. 1989).

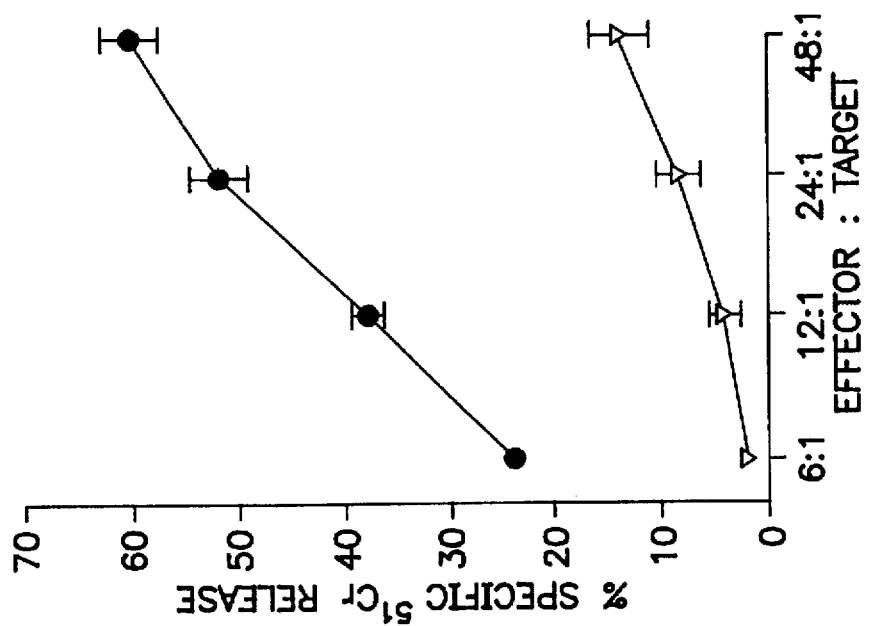
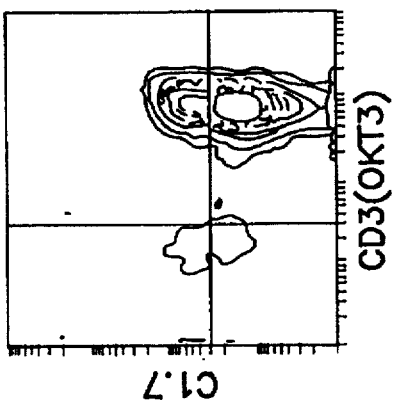
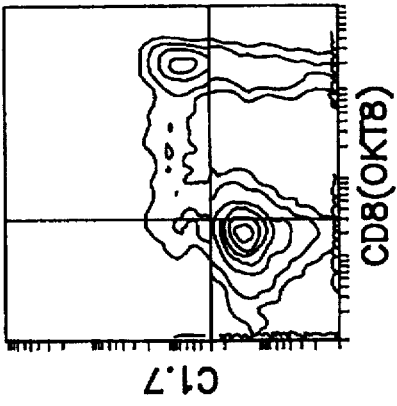
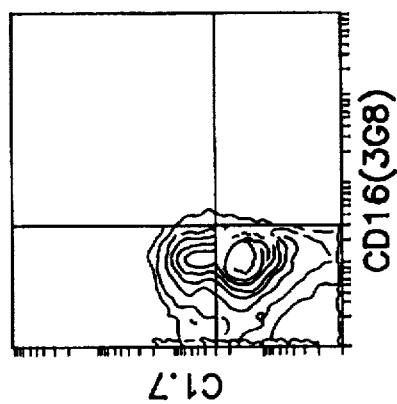
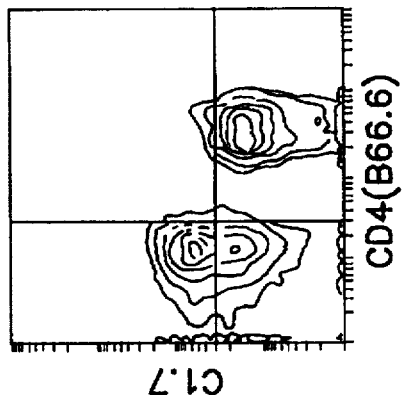

HUMAN CYTOTOXIC LYMPHOCYTE SIGNAL TRANSDUCTION SURFACE PROTEIN (P38) AND MONOCLONAL ANTIBODIES THERETO

The United States government has certain rights in this invention through the funding provided by U.S. Public Health Service grants CA-10815, CA-20833, CA-32898, CA-40256 and NIH grant CA-09171.

FIELD OF THE INVENTION

The present invention relates to the field of monoclonal antibodies and their receptors. More specifically, this invention relates to monoclonal antibodies capable of binding an antigenic receptor on Natural Killer (NK) cells and T cells.

BACKGROUND OF THE INVENTION

Cytotoxic lymphocytes are a critical effector arm of cell-mediated immune responses to intracellular parasitic infections, both bacterial and viral, and tumors. Among such cytotoxic cells are included cytotoxic $CD8^+$ T cells and natural killer (NK) cells. $CD8^+$ cytotoxic T lymphocytes (CTL) recognize target cells by at least two distinct mechanisms.

The first mechanism, "major histocompatibility complex (MHC)-restricted cytotoxicity", involves the interaction of CTL with the target cell via highly specific recognition of the MHC class I, or less frequently, class II and antigenic peptides by clonally distributed T cell antigen receptor (TCR). MHC-restricted cytotoxicity effectors also elicit memory [R. M. Zinkernagel et al., Nature (Lond), 251:547–548 (1974)]. For example, $CD8^+$ cells mediate the MHC class I restricted lysis of infected or altered host cells and the production of interferon gamma and tumor necrosis factor [G. Le Gros et al, Curr. Opin. Immunol., 6(3):453–457 (June 1994)].

In contrast, the second mechanism called "non-MHC-restricted cytotoxicity", is mediated primarily by $CD3^-$, $CD16^+$ and $CD56^+$ NK cells which recognize target cells through possibly multiple and heterogenous interactions of receptor/ligand pairs that are not directly restricted by MHC recognition [L. L. Lanier et al, J. Immunol., 137:2735 (1986)]. Although non-MHC restricted cytotoxic effectors are less specific than CTL and do not generate immunologic memory responses, their early activation during an immune response and their broad lytic abilities make them an important effector component of natural resistance, active as a first line of defense well before specific effector mechanisms are elicited.

Resting NK cells express a number of surface molecules which, when stimulated, can activate the cytotoxic mechanism. These surface molecules, or receptors, include CD16, which is the low affinity Fc receptor of IgG expressed by virtually all human NK cells, as well as a minor population of T cells [see, e.g., G. Trinchieri, Adv. Immunol., 47:187 (1989); B. Perussia et al, J. Immunol., 133:180 (1984)]. Another NK antigen, CD2, is expressed by 80–90% of NK cells and recognizes CD58 or CD59 ligands on target cells, and can also activate NK cells cytolytically [R. F. Siliciano et al, Nature (Lond), 317:428 (1985); C. Anasetti et al, J. Immunol., 139:1772 (1987); W. C. Hahn et al, Science, 256:1805 (1992)]. Neither CD16 nor CD2 appear to be required for non-MHC-restricted cytotoxicity. NK cells that lack either molecule can still mediate natural killing [G. Trinchieri, cited above; L. L. Lanier et al, J. Immunol., 141:3478 (1988)].

Other surface molecules with unknown ligands have recently been identified on NK cells that can also activate cytotoxicity. These include NKRP1 on rat NK cells [W. H. Chambers, et al, J. Exp. Med., 169:1373 (1989); R. Giorda et al, Science, 249:1298 (1990)]; NK1.1 antigen expressed by murine NK cells [F. M. Karlhofer et al, J. Immunol., 146:3662 (1991); J. C. Ryan et al, J. Immunol., 149:1631 (1992); and NKG2 which, in humans, codes for putative polypeptides displaying homology with NKRP1 [J .P. Houchins et al, J. Exp. Med., 173:1017 (1991)]. Additional molecules include pNKR1 [J. L. Frey et al, J. Exp. Med., 174:1527 (1991); the molecules reactive with mAbs 5C6 and 6D3.2 [Evans et al, J. Immunol., 141:324 (1988); Harris et al, Proc. Natl. Acad. Sci., USA, 88:3009 (1991) and Evans et al, Scand. J. Immunol., 37:131 (1993); and the surface molecule identified by mAb PP35 [Moretta et al, Int. J. Cancer, Suppl. 7:6–10 (1992)]. Other NK cell receptors are described in U.S. Pat. No. 5,229,494.

NK cells are potent producers of lymphokines, and this activity can be induced by many stimuli that also activate their lytic mechanisms, such as perturbation of FcγRIII (CD16) [M. A. Cassatella et al, J. Exp. Med., 169:549 (1989); I. Anegon et al, J. Exp. Med., 167:452 (1988); M. J. Smyth et al, J. Immunol., 146:3815 (1991)].

Cell surface markers are also used to characterize T cell populations. For example, CD8 is a surface marker of the cytotoxic $CD8^+$ cells. CD4 is a surface marker of the helper T cells of the same name. Other T cell surface receptors, generally designated by the monoclonal antibodies which bind them, include CD3, CD28, CD5 and/or CD2, and others described in the literature.

It has long been known that $CD4^+$ T cells can be subdivided into two subsets of helper cells: Th1 cells which produce cytokines and factors capable of promoting delayed-type hypersensitivity reactions characteristic of cell-mediated immunity, and Th2 cells which direct humoral immune responses, promote allergic type responses and generally suppress inflammatory responses [A. O'Garra et al, Curr. Opin. Immunol., 6(3): 458–466 (June 1994)]. However, it has only recently been reported that there may be similar subsets of $CD8^+$ cells, based on reports of the ability of $CD8^+$ cells to switch effector functions. For example, disease progression in AIDS has been linked to the loss of $CD8^+$ T cell cytotoxic activity and the subsequent appearance of Th2 type (i.e., regulatory or suppressor) effector activities [see, e.g., Le Gros et al and O'Garra et al, both cited above].

Although a few surface molecules have been identified that may have a role in spontaneous cytotoxicity, the mechanism by which NK cells and other non-MHC-restricted cytotoxic cells recognize target cells still remains poorly defined, and it is likely that multiple mechanisms may exist. Further, to date, none of the known surface molecule receptor-ligand pairs has demonstrated the ability to distinguish activated (cytotoxic) NK cells from resting NK cells, or to distinguish between CD4 cell subsets, or between the two putative CD8 cell subsets.

There is thus a need in the art for the identification of new cytotoxic lymphocyte cell surface antigens or receptors, as well as ligands thereto for use in both therapeutic and diagnostic regimens.

SUMMARY OF THE INVENTION

In one aspect, the invention provides a novel 38 kD signal transduction surface molecule (p38) expressed by virtually all human NK cells, i.e., $CD3^-$, $CD16^+$, $CD56^+$, as well as by subpopulations of T cells comprising approximately half of CD8+ (α/β+ TCR) T cells and TCR γ/δ+ T cells. The inventors have determined that this receptor can serve as an activation marker for cytotoxic NK cells, and both an activation and identification marker of the subset of cytotoxic CD8+ cells analogous to Th1 cells.

In another aspect, the invention provides a ligand capable of binding to, and activating, the p38 receptor. One such ligand is the murine monoclonal antibody, mAb C1.7. C1.7 binds to the p38 receptor on NK cells and cytolytic CD8+ cells, and can activate these cells. The hybridoma cell line secreting mAb C1.7 is also provided.

In still another aspect, there is provided a diagnostic method for identifying or monitoring a disease characterized by the presence, absence, or progressive depletion of cytotoxic CD8+ cell levels by measuring the number of CD8+ T cells bearing the p38 receptor in a patient. One such disease is AIDS. This method involves exposing a patient sample, e.g., peripheral blood lymphocytes (PBL), to a known amount of a p38 ligand, e.g., mAb C1.7, and determining the number of p38+ CD8+ T cells, or the ratio of p38+ to p38− CD8+ T cells. Such measurement may be accomplished by conventional techniques such as flow cytometry.

In another aspect, this invention provides a method of stimulating the immune response by manipulating the amounts of p38+ or p38− CD8+ T cells in a patient. Such manipulation may include identification and separation of cells expressing or not expressing the p38 receptor ex vivo and reintroducing the desired subset back into the patient. Alternatively, a ligand to p38 may be employed to prevent or reduce the cytotoxic activity of p38+ cells in diseases characterized by overexpression of such cells.

In yet another aspect, the invention provides a bispecific antibody comprising a p38 antigen targeting region, e.g., derived from mAb C1.7 (or another p38 ligand), and a second antigen targeting region, e.g., a region directed to any tumor antigen or viral antigen expressed on the cell surface. This bifunctional antibody is characterized by the biological activity of mAb C1.7.

Other aspects and advantages of the present invention are described further in the following detailed description of the preferred embodiments thereof.

BRIEF DESCRIPTION OF THE DRAWINGS

FIGS. 1A(i), 1A(ii), 1A(iii), and 1A(iv) depict two-color immunofluorescence analyses performed with anti-CD16, anti-CD3, anti-CD4, and anti-CD8 antibodies, respectively, on rIL-2-cultured (5 day) NK-depleted lymphocytes from a representative donor.

FIG. 1B is a graph plotting E:T ratio vs. % $^{51}$Cr release with cultured lymphocytes depleted of CD4+ cells (●) or CD4+ and p38+ cells (▽) used as effectors in 3 hour chromium release assay against $^{51}$Cr-labeled Daudi targets. Results are presented as the mean percentage of specific $^{51}$Cr release±SE (n=4).

DETAILED DESCRIPTION OF THE INVENTION

Figure 2C:
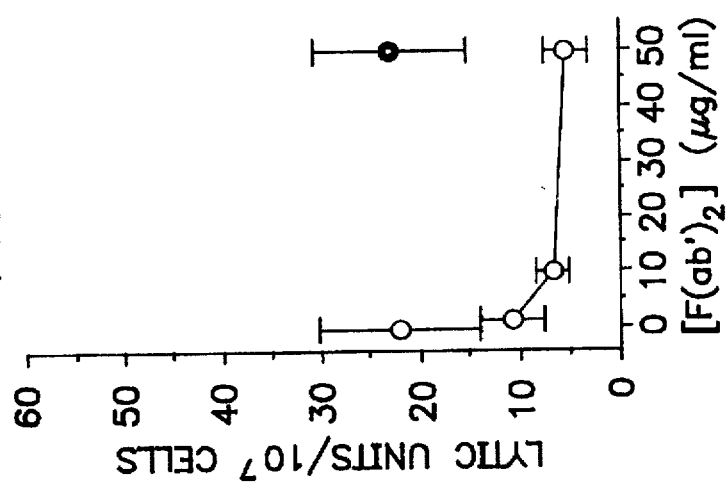
FIG. 2C is a graph demonstrating the results of an assay similar to that of FIG. 2B, except that $^{51}$Cr-labeled Daudi cells were the target. Symbols and results are as reported in FIG. 2A.

The present invention provides a novel signal-transducing surface molecule, i.e., a receptor protein called p38, which is expressed by lymphocyte subsets capable of cell-mediated cytotoxicity. Ligands capable of binding to the novel receptor and methods for use of the receptor and ligands are also disclosed.

I. The Receptor and MAb C1.7

The novel receptor, p38, has been found by the inventors to be present on virtually all human CD3−/CD16+/CD56+ natural killer (NK) cells. Further, subpopulations of T cells comprising approximately half of CD8+ (T cell receptor [TCR] α/β+) T cells and TCR− γ/δ+ T cells express the p38 surface molecule. These T cell subpopulations are lymphocyte subsets capable of cell-mediated cytotoxicity. p38 has a direct role in the recognition, signal transduction, and/or lytic mechanisms of non-MHC-restricted cytotoxicity. More specifically, this receptor protein can serve as an activating structure for cytotoxic NK cells, and as both an activating and identification marker of the subset of cytotoxic CD8+ cells.

The novel receptor of the present invention was initially identified by its ability to bind to a selected ligand, the novel monoclonal antibody C1.7. The C1.7 antibody producing hybridoma was selected from a panel of hybridomas obtained by fusion of spleen cells from human NK-immunized BALB\c mice with the BALB\c myeloma cell line PX63.Ag8.653 on the basis of its ability to be efficiently lysed by NK effector cells in a chromium release assay. The production of mAb C1.7, is described in detail in Example 1 below. The hybridoma which secretes mAb C1.7 was deposited with the American Type Culture Collection, 12301 Parklawn Drive, Rockville, Md., U.S.A. under accession number ATCC HB-11717 on Sep. 14, 1994. This deposit complies with the requirements of the Budapest Treaty. Any restrictions to access of these materials will be removed upon grant of a patent on this subject matter.

MAb C1.7 is a soluble IgG1 antibody which induces NK cell-mediated, antibody-redirected lysis of murine mastocytoma FcγR+ target cells, indicating that the surface molecule recognized by mAb C1.7 is an activating structure on NK cells. MAb C1.7 was found to strongly react with about 24% of lymphocytes, weakly react with monocytes, and not react with granulocytes as determined by single-color immunofluorescence. The surface phenotype of the lymphocyte populations reacting with mAb C1.7 was identified by two-color immunofluorescence. MAb C1.7 reacted with almost all CD16+ and CD56+ NK cells and with about 50% of CD3+/CD8+ T cells, as described in detail in Example 3 below. When examined during the 5th International Conference on Human Leukocyte Differentiation Antigens, Boston, Mass. in Nov. 1993 and compared in encoded form with other antibodies, C1.7 was not given a cluster designation. No other antibody was found to recognize the same structure as that recognized by C1.7. mAb C1.7 is a distinct antibody from all other known antibodies to T cell/NK receptors.

The mAb was employed in a Western blot to isolate its receptor by binding and permit its identification by molecular weight. As reported in Example 4 below, the p38 receptor is apparently a monomer which runs in an SDS gel, under both reducing and non-reducing conditions, at a molecular weight of about 38,000.

Thus, the mAb C1.7 was employed to identify functional characteristics of the novel p38 receptor in a number of assays which are described in detail below. See, Valiante and Trinchieri, *J. Exp. Med.*, 178:1397 (October 1993), incorporated by reference herein.

A. Stimulation of p38 Results in Activation of Cytotoxicity.

A variety of chromium release assays were performed to demonstrate that this p38 receptor was stimulated on NK cells with the mAb C1.7 and activated NK cell-mediated redirected cytotoxicity. In the antibody-redirected lysis assays described in Example 5, mAb C1.7 was found to increase cultured and fresh NK cell-mediated antibody redirected lysis of target cells in a manner similar to that of an anti-CD16 antibody.

However, unlike other NK cell surface molecules that activate cytotoxicity, p38 stimulation did not result in the release of the granule enzyme N-carbobenzoxy-L-thiobenzyl ester-esterase (BLT esterase) even under conditions in which mAb C1.7 induced NK cell-mediated redirected lysis of $Fc\gamma R^+$ target cells. Because BLT-esterase release is associated with NK cell degranulation, the lack of BLT-esterase release from NK cells mediating mAb C1.7-redirected lysis indicates that the cytotoxic mechanism induced by p38 stimulation may not involve extensive granule release. It has recently been demonstrated that non-MHC-restricted cytotoxicity mediated by resting and rIL-2-activated NK cells occurs through distinct mechanisms, in that rIL-2-activated, NK cell-mediated cytotoxicity appears independent of BLT-esterase release [M. Clement et al, *Eur. J. Immunol.*, 23:697 (1993)]. The demonstration, described in Example 6 below, that mAb C1.7-redirected lysis does not involve BLT-esterase release indicates that mAb C1.7-induced cytotoxicity may occur through a similar mechanism.

B. p38 Differs from CD16 in BLT-Esterase Release

Although there is another molecule with these characteristics on human NK cells, which is known to the prior art as $Fc\gamma RIIIA$ or CD16, stimulation of NK cells with anti-CD16 mAb or CD16 ligands (immune complexes) results in activation of cell-mediated cytotoxicity as well as release of BLT-esterase and lymphokines. p38-mediated activation of NK cell cytotoxicity differs from CD16 activation. p38 stimulation, under conditions that induced NK cell Cytotoxic activity equal to or greater than that observed for CD16 stimulation, did not result in the release of the granule enzyme BLT-esterase.

C. p38 Mediates Signal Transduction

Another functional characteristic of the interaction of mAb C1.7 and the receptor p38, was that upon crosslinking of the mAb and the receptor on purified culture NK cells, polyphosphoinositide turnover was increased, as was $[Ca^{2+}]_i$. This demonstrated that signal transduction occurs through the receptor of the mAb C1.7. However, this investigation of the signal transduction pathways induced by p38 stimulation did not demonstrate any obvious difference between p38-mediated and CD16-mediated signal transduction that would account for p38's inability to initiate BLT-esterase release. Both p38 and CD16 stimulation resulted in the rapid hydrolysis of phosphatidylinositol 4,5-bisphosphate ($PIP_2$) and increases in $[Ca^{2+}]_i$, as well as activation of phospholipase D. Unlike CD16-mediated signal transduction, which is directly activated at low levels by soluble anti-CD16 antibodies and is substantially enhanced after cross-linking, p38-mediated signal transduction was observed only after crosslinking of $F(ab')_2$ fragments of mAb C1.7 with $F(ab')_2$ fragments of a goat anti-mouse Ig (GαMIg). No signal-transducing activity of p38 was demonstrated on fresh and short-term cultured (rIL-2 or rNKSF/IL-12) T cells. However, leukemic T cell lines (TALL 103/2 [$TCR^-\gamma/\delta^+$] and TALL 104 [$TCR-\alpha/\beta^+$]) that express p38 and exhibit non-MHC-restricted cytotoxic activity were shown to mediate mAb C1.7-redirected lysis.

D. p38 Stimulation Induces Lymphokines

MAb C1.7 is also capable under certain conditions of inducing lymphokine production, particularly IFN-γ and IL-8, from cultured NK cells. Similar to CD16-induced lymphokine production, the C1.7 induction was maximal in the presence of other lymphokine-inducing stimuli such as rNKSF/IL-12 or rIL-2. For example, in the presence of IL-2 or IL-12, the mAb induced increased production of IFN-γ; however, the mAb alone induced IL-8. See, e.g., Example 7 below. Unlike anti-CD16-induced cytokine production, which is stimulated by antibodies presented on any solid support, p38-stimulated IFN-γ and IL-8 production only occurred when mAb C1.7 was presented to the NK cells by an $Fc\gamma R^+$ cell line.

E. p38 Stimulation Affects Lymphocyte Proliferation

Additionally, the mAb also demonstrated the ability to modulate lymphocyte (i.e., NK cell) proliferation when in the presence of IL-12 or IL-2. As described in detail in Example 8, the treatment of fresh PBL with soluble mAb C1.7 resulted in enhanced thymidine uptake in the presence of rNKSF/IL-12 and rIL-2. However, no consistent expansion of the number of $C1.7^+$ cells in the cultures of $p38^+$ cell subsets was observed when compared with untreated controls. On cultured NK cells, mAb C1.7 treatment was antagonistic to rNKSF/IL-12-induced and rIL-2-induced proliferation, similar to that observed for anti-CD16 (mAb 3G8) treatment. The opposing effects of p38 stimulation on these lymphocyte preparations may indicate that p38 modulates proliferation differently depending on the cell type or level of activation.

F. p38 is a Marker for Cytotoxic $CD8^+$ T Cells

Additional experiments were conducted which demonstrated that activated (rIL-2, 5 day) $CD8^+$ T cells mediated non-MHC-restricted cytotoxicity, and that the $CD8^+/p38^+$ subset contained the overwhelming majority of this activity. As described in detail in Example 10, because p38 is expressed by ~50% of fresh $CD8^+$ T cells, $p38^+$ and $p38^-$ $CD8^+$ T cells obtained from PBL cultured for 5 days in the presence of rIL-2, differed in their ability to mediate non-MHC-restricted cytotoxicity. On rIL-2-cultured (5 day) $CD8^+$ T cells, only $p38^+$ and not $p38^-$ T cells had the ability to lyse a variety of NK cell-sensitive and -resistant tumor derived or virally infected target cells. Further, cultured (rIL-2; 5 day) CD16/CD56-depleted and CD4-depleted $CD8^+$ T cells displayed a high level of non-MHC-restricted cytotoxic activity. These results demonstrate that depletion of the $p38^+$ population from these cultured $CD8^+$ T cells almost completely abolishes this activity.

Recent data using highly enriched or clonal populations of either $p38^+$ or $p38^-$ $CD8^+$ T cells suggests that $p38^+$ $CD8^+$ T cells are the cytotoxic, high gamma interferon/low IL-4/low IL-10 producing cells. In contrast, $p38^-$, $CD8^+$ T cells are less cytotoxic and produce high levels of IL-4, IL-10 and low levels of gamma interferon. This split may be critical in analyzing the progress and treatment of HIV patients, where $p38^+$ populations may be important in long term survival. Both $p38^-$ and $p38^+$ $CD8^+$ cells produce similar amounts of TNF and GM-CSF.

Thus, p38 is a marker for non-MHC-restricted cytotoxic T cells and also may be required for this activity. p38 expression identifies the subset of cytotoxic lymphocytes (NK cells) in fresh PBL capable of non-MHC-restricted cytotoxicity and a functionally similar subset in rIL-2-cultured CD8⁺ T cells. The shared expression of p38 by NK cells and non-MHC-restricted cytotoxic T cells indicates that p38 may be involved in a common cytotoxic mechanism utilized by these distinct effector cell populations. Given that p38 is present on both fresh and activated CD8⁺ T cells, other activation events may also be required for the generation of non-MHC-restricted cytotoxic T cells.

G. p38 Enables Target Cell Recognition

The effects of F(ab')$_2$ fragments of antibodies directed against cytotoxic lymphocyte surface molecules can be either enhancing or inhibitory to cytotoxicity, depending on the type of surface molecule recognized by the antibody. It has been postulated that F(ab')$_2$ fragments of antibodies directed against activating structures or adhesion molecules inhibit cytotoxicity, whereas F(ab')$_2$ fragments of antibodies directed against inhibitory receptors enhance cytotoxicity, perhaps by blocking the delivery of a negative signal [See, e.g., W. M. Yokoyama, Curr. Opin. Immunol., 5:67 (1993)].

F(ab')$_2$ fragments of mAb C1.7, prepared as described in Example 2, were shown to substantially inhibit non-MHC-restricted cytotoxicity mediated by fresh PBL and rIL-2-activated T cells. These findings suggest that p38 has a role in target cell recognition by these non-MHC-restricted cytotoxic cells and cell-mediated cytotoxicity. However, these fragments did not affect spontaneous cytotoxicity mediated by activated, cultured NK cells, suggesting that once activated, NK cells may utilize multiple or alternative mechanisms for cytotoxicity.

H. p38 Differs from other Surface Molecules.

The p38 surface molecule identified by mAb C1.7 appears to be an activating structure on cytotoxic lymphocytes and NK cells, similar in this ability to other previously identified surface molecules, but distinct from these other molecules based on its unique leukocyte distribution and structure. It is also distinct from other known NK cell and T cell surface antigens on the basis of activation studies and immunofluorescence analysis.

Other phenotypic differences between these p38⁺ and p38⁻ T cell populations also exist. See Example 13 for a comparison of surface distribution of p38 and three other cell surface markers, S6F1 (anti-LFA-1 epitope), CD29 and CD28, which have been used to distinguish between CD8⁺ T cell populations with high and low cytotoxic potential. Such comparisons have shown that no other antigen markers have been described with the precise distribution of p38.

II. DNA and Protein Sequences of p38

The DNA and protein sequences for the receptor p38 may be obtained by resort to conventional methodologies known to one of skill in the art. For example, the receptor may be isolated by immunoprecipitation using the mAb C1.7. Alternatively, the receptor may be obtained by prokaryotic expression cloning, using the lambda phage gt11, which is described in detail in Sambrook et al, Molecular Cloning. A Laboratory Manual., 2d edit., Cold Spring Harbor, N.Y. (1989), pp. 2.43–2.84, incorporated by reference herein.

Additionally, as described in Example 12 below, the DNA sequence encoding the receptor can be obtained by the "panning" technique of screening a human NK cell library by eukaryotic expression cloning, of which several are known. Briefly, plasmids are constructed containing random sequences of a human NK cell library which are obtained by restriction digestion. Such libraries may be made by conventional techniques or may be available commerically.

Suitable cells, preferably mammalian cells, such as COS-1 cells, are transfected with the plasmids and the mAb C1.7 antibody employed to identify transfectants containing the receptor after repeated rounds of panning. The receptor insert in these cells is then identified and sequenced by conventional techniques, such as overlapping deletion fragments [Sambrook et al. cited above]. Other known techniques may also be employed to sequence the receptor and/or the mAb C1.7.

III. Utilities of p38 and MAb C1.7

A. Use of p38 in the Identification of Other Ligands

Because p38 is involved in cell-mediated cytotoxicity, it is likely that ligands of p38 are expressed by a number of NK-sensitive targets. The restricted expression of p38 to cells with non-MHC-restricted cytotoxic activity, its ability to activate these cells cytolytically, and the fact that F(ab')$_2$ fragments of the anti-p38 antibody C1.7 inhibit the spontaneous cytotoxic activity of some effector populations, suggest that the p38 surface molecule is directly involved in the mechanisms of non-MHC-restricted cytotoxicity.

Thus, the p38 receptor may itself have utility in identifying other ligands, by conventional methods such as isolating other ligands from biological samples by binding to a column. The receptor may be employed directly as a antigen to obtain or identify antibodies or other ligands in addition to mAb C1.7.

B. Therapeutic Uses of p38

If soluble, the p38 receptor (or its antibodies) may be employed therapeutically to block ligands to CD8 cells, which mediate transplant rejections. This blocking has been shown to inhibit CD8 T cell killing of targets and can be used in situations where one would want limited CD8 activity, such as transplantation rejection or CD8-mediated cell autoimmune destruction.

C. Diagnostic Uses of p38

Further, the receptor may be employed in methods to distinguish between cytotoxic CD8⁺ and CD8⁻ cell subsets and enable the measurement, as well as the manipulation, of such cells in a subject experiencing, or being treated for, a disease in which the emergence of one subset over another is indicative of disease progression, e.g., AIDS. As noted by O'Garra et al, cited above, the ability to recognize such subsets of CTLs may permit eventually the potential to induce a response appropriate for a specific pathogen, with minimum pathology.

D. Diagnostic Uses of C1.7

The mAb C1.7 as a p38 ligand also has a number of utilities. For example, mAb C1.7 may be employed in a diagnostic or prognostic method for identifying T cell subset dysregulation in pathology, or in monitoring a disease characterized by the presence, absence, or progressive depletion of cytotoxic CD8⁺ cell levels. This method involves using the p38 ligand to measure the number of CD8⁺ T cells bearing the p38 receptor in a patient. This method involves exposing a patient sample, e.g., PBLs, to a known amount of a p38 ligand, e.g., mAb C1.7, in an appropriate assay method. The number of p38⁺ CD8⁺ T cells, om the ratio of p38⁺ to p38⁻ T cells may then be measured. Such measurement may be accomplished by conventional techniques such as flow cytometry. By studying the change in the absolute number or, preferably, the ratio of these cells, the progress of disease and/or the progress of therapy can be measured where CD8⁺ cells may be a factor.

One obvious disease suitable for such a diagnostic effort is AIDS; although it is anticipated that other diseases, including other viral infections, bacterial or parasitic infections, autoimmunity and cancers, may also be suitable candidates for such a method.

E. Therapeutic Uses of C1.7

The p38 ligand, C1.7, may also be employed in a method for stimulating the immune response by separating the CD8+ T cell subsets and reintroducing a desired subset into patients. For example, C1.7 is useful in manipulating the amounts of p38+ or p38− CD8+ T cells in a patient. Such manipulation may include identification and separation of cells expressing or not expressing the p38 receptor ex vivo using the p38 ligand. Once separated and identified as p38+ CD8+ or p38− CD8+, the CD8+ cell subset may be activated by exposure to the ligand or an activating substance, e.g., a cytokine or lymphokine, and reintroduced into the patient to fight viral infections, among others. Alternatively, the p38−, CD8+ T cells which have suppressor activity may be separated from the cytotoxic p38+, CD8+ cells, cultured and reintroduced into the patient. This would be suitable in inhibiting unwanted immune responses, such as in transplantation or autoimmunity. A ligand to p38 may also be employed in vivo to prevent or reduce the cytotoxic activity of p38+ cells in diseases characterized by overexpression of such cells. Thus, ligands to p38, such as mAb C1.7 have utility in both the diagnosis and treatment of immunosuppression, transplantation or autoimmune diseases.

F. Preparation of Bispecific Antibodies

Additionally, mAb C1.7 or another p38 ligand is useful in the generation of bispecific or chimeric antibodies. Bifunctional antibodies, also referred to as bispecific or heterobispecific antibodies, are produced by combining two different monoclonal antibodies which recognize two different antigens, so that the ability to bind to the two different antigens resides in one molecule. Bifunctional antibodies use the ability of one antibody to bind to the target cells (e.g., a mAb against a tumor-associated antigen) and of another antibody directed against a cytotoxicity-triggering receptor on cytotoxic effector cells [B. Karpovsky et al, *J. Exp. Med.*, 160:1068 (1984).

A bifunctional antibody of this invention may be constructed using various conventional techniques (see Example 14).

Such bifunctional antibodies are employed to modulate cytotoxic lymphocyte activity in patients with cancer or incurable and debilitating vital infections. Such antibodies are useful to activate and target p38+ cytotoxic cells to virally infected cells and neoplastic cells. For example, a bifunctional antibody can be prepared with binding sites for a tumor cell surface antigen and for the signal transducing molecule p38 on cytotoxic CD8+ T cells. The two specificities are joined in a single molecule that cross-link the effector to the target cells and at the same time trigger the cytotoxic (lytic) mechanism, thereby activating the cytotoxic mechanism of the T cells in the vicinity of specific tumor cells. This has been accomplished with bifunctional antibodies produced using either anti-CD3 or anti-CD16 antibodies [A. Lanzaveccia and D. Scheidegger, *Eur. J. Immunol.*, 17:105 (1987); J. A. Titus et al, *J. Immunol.*, 139:3153 (1987)], which have demonstrated the ability to prevent growth of human tumors in conjunction with human lymphocytes injected in vivo in nude mice.

The following examples illustrate the preferred compositions and methods for obtaining mAb C1.7, determining the characteristics of the p38 receptor and its ligand, and isolating and characterizing its receptor. In view of this disclosure, it will be clear to one of skill in the art that other methods for obtaining the antibody and receptor are available and are therefore encompassed in this invention. These examples are illustrative only and do not limit the scope of the invention.

EXAMPLE 1 mAb C1.7 Preparation 6-wk-old female BALB/c mice were immunized intraperitoneally with $20 \times 10^6$ purified, cultured human NK cells, followed by four intraperitoneal injections of NK cells in a 5 month period. The animals were then injected intravenously with the same amount of NK cells and after 3 days the mice were killed and a spleen cell suspension was prepared and fused with the BALB/c myeloma cell line P3X63.Ag8.653 [ATCC CRL 1580]. The fused cells were cloned by limiting dilution and the resultant hybridomas were labeled with $^{51}Cr$ and screened for their ability to activate NK cell cytotoxicity in a standard 3 hour chromium release assay. The C1.7 hybridoma producing the IgG1 C1.7 antibody was selected for further study on the basis of its ability to be efficiently lysed by the NK effector cells.

EXAMPLE 2

Sources of Materials

A. The cell lines

The human Burkitt lymphoma-derived cell line Daudi [ATCC #CCL213], the EBV-transformed cell line RPMI-8866 [Roswell Park Memorial Institute, Buffalo, N.Y.], the erythromyeloid leukemia cell line K562 [ATCC #CCL243], the murine mastocytoma (FcγR+) cell line P815X2, and the murine antibody-secreting hybridomas were maintained in culture in RPMI-1640 medium (Flow Laboratories, Inc., McLean, Va.) supplemented with 10% fetal bovine serum (FBS) (Flow Laboratories, Inc.). All cell lines were free of mycoplasma contamination on repeated testing.

B. The monoclonal antibodies

Antibodies used were OKT3 (IgG2a, anti-CD3), B36.1 (IgG2b, anti-CD5), 3G8 (IgG1, anti-CD16), B73.1 (IgG1, anti-CD16), B159.5 (IgG1, anti-CD56), B52.1 (IgM, anti-CD14), B66.6 (IgG1, anti-CD4), B116.1 (IgG2a, anti-CD8), OKT8 (IgG2a, anti-CD8), TCR-δ1 (anti-TCR δ chain), TIA-2 (anti-CD3ζ), B133.1 and B133.5 (both IgG1, anti-IFN-γ), Mc.a-NAP-1 (Anti-IL-8), and Pc.a-NAP-1 (goat anti-human IL-8 antibody). Antibody 3G8-producing cells were kindly provided by Dr. J. Unkeless (Mount Sinai School of Medicine, New York, N.Y.); OKT3, OKT4, and OKT8 cells were obtained from the American Type Culture Collection (Rockville, Md.); antibody TCR-δ1 was kindly provided by Dr. M. Brenner (Harvard University, Boston, Mass.), antibody TIA-2 was provided by Dr. P. Anderson (Dana Farber Cancer Institute, Boston, Mass.), and the anti-IL-8 antibodies were a generous gift from Dr. M. Ceska (Sandoz Inc., Vienna, Austria); all other antibodies were produced and characterized in the inventors' laboratory.

C. Cytokines

Chinese hamster ovary cell-derived rNKSF/IL-12 was kindly provided by Dr. S. Wolf (Genetics Institute, Boston, Mass.), and rIL-2 ($10^7$ U/mg) was provided by Dr. T. Taguchi (Osaka University and Takeda Chemical Industry, Inc., Osaka, Japan).

D. PBL Cultures

Peripheral blood mononuclear cells (PBMC) were obtained from peripheral blood by Ficoll-Hypaque density gradient centrifugation followed by a 1 hour incubation in plastic flasks to partially deplete adherent monocytes. Cultured NK cells were prepared as described in B. Perussia et al, *Natl. Immun. Cell. Growth Requl.*, 6:171 (1987) with some modifications. Briefly, PBL were cultured in 24-well plates (Nunclon, Roskilde, Denmark) at $2.5 \times 10^5$ cells/ml in RPMI-1640 medium with 10% fetal bovine serum (FBS) at 37° C. in a 9.5% $CO_2$ atmosphere together with the irradiated (50-Gy) RPMI-8866 B cell line ($5\times10^4$ cells/ml). On day 6 of culture, half of the medium was replaced with fresh RPMI-1640/10% FBS and all cultures were collected on days 8–10. NK cells (>98% $CD16^+/CD56^+/CD3^-$) were purified from 8–10 day cultures by depletion of T cells and monocytes by antiglobulin rosetting with the mAbs OKT3, B36.1, and B52.1. Non-MHC-restricted cytotoxic $CD8^+$ T cells were obtained from rIL-2 (200 U/ml)-cultures (5 d) PBL that were depleted of NK cells and monocytes by antiglobulin rosetting using mAbs 3G8, B73.1, B159.5, and B52.1 at the start and end of cultures. At the end of culture, the NK-depleted PBL were subjected to two color immunofluorescence analyses and depleted of $CD4^+$ cells or $CD4^+$ and $C1.7^+$ cells by antiglobulin rosetting with mAb B66.6 or with mAbs B66.6 and C1.7, respectively.

E. $F(ab')_2$ Fragments mAbs C1.7 and 3G8 (1 mg/ml) purified by affinity chromatography on a protein G column (Pharmacia Fine Chemicals, Upsala, Sweden) were digested with pepsin (0.05%; Sigma Chemical Co., St. Louis, Mo.) for 18 h at 37° C. in 0.1M sodium acetate, pH 4.1. Pepsin digests were dialyzed against PBS and subjected to protein G column chromatography to remove undigested IgG. Commercially obtained goat anti-mouse Ig (Gα MIg) $F(ab')_2$ fragments (Cappel Laboratories, Cochranville, Pa.) were also passed through a protein G column to remove possible contaminating IgG. All column effluents were confirmed to consist of pure $F(ab')_2$ fragments by SDS-PAGE followed by silver staining.

EXAMPLE 3 mAb C1.7 Reactivity with Leukocyte Subsets

Single-color indirect immunofluorescence analyses (flow cytometry) of human peripheral blood leukocytes (PBLs) indicated that $24.4\pm2.9\%$ (mean±SE [n=12]) of lymphocytes were reactive with mAb C1.7. Monocytes stained with much lower fluorescence intensity than lymphocytes with mAb C1.7, whereas granulocytes were negative for mAb C1.7 reactivity.

The surface phenotype of lymphocyte populations was determined by two-color immunofluorescence with mAbs using an EPICS Elite cytofluorograph (Coulter Corp., Hialeah, Fla.). mAbs were either biotinylated (biotin-N-hydroxysuccinimide ester; Calbiochem-Novabiochem Corp., La Jolla, Calif.) or directly conjugated to FITC (International Biological Supplies, Melbourne, Fla.) according to the manufacturer's instructions. Biotinylated reagents were detected with phycoerythrin Streptavidin (PE-Avidin; Coulter Corp.).

The two-color immunofluorescence analyses were performed on PBL preparations from 10 donors. The PBL used in the analyses were (a) not stained with antibody; (b) stained with biotinylated mAb C1.7 (detected with PE-avidin) and simultaneously with FITC-conjugated anti-CD16 (3G8); (c) stained with biotinylated mAb C1.7 (detected with PE-avidin) and simultaneously with anti-CD3 (OKT3); (d) stained with biotinylated mAb C1.7 (detected with PE-avidin) and simultaneously with anti-CD4 (B66.6); (e) stained with biotinylated mAb C1.7 (detected with PE-avidin) and simultaneously with anti-CD8 (B116.1); (f) depleted of $CD16^+$, $CD56^+$, $CD4^+$ cells before analysis and not stained with antibody; or (g) depleted of $CD16^+$, $CD56^+$, $CD4^+$ cells before analysis and stained with mAb C1.7 and anti-TCR-δ (TCR-δ1).

In all experiments, mAb C1.7 reacted with virtually all $CD16^+$ and $CD56^+$ NK cells and with $51.6\pm5.2\%$ (range: 29.9–73.2%; n=10) of $CD3^+/CD8^+$ T cells. mAb C1.7 reactivity was never observed on $CD4^+$ T cells.

To analyze mAb C1.7 reactivity with fresh peripheral blood $\gamma/\delta^+$ T cells, which in most donors comprise a very low percentage of lymphocytes, PBL from five donors were depleted of $CD16^+$, $CD56^+$, and $CD4^+$ lymphocytes by antiglobulin rosetting and analyzed by two-color immunofluorescence. In these preparations TCR-$\gamma/\delta^+$ cells represented $21.2\pm9.1\%$ (n=5) of the total lymphocytes, and $62\pm6\%$ (range: 45.1–81.7%) of these T cells were mAb $C1.7^+$. The intensity of mAb C1.7 staining and its reactivity with different lymphocyte subsets were unaffected by activation or culture conditions. Activated NK cells from 8 day culture with certain EBV-transformed B cell lines, activated $\gamma/\delta^+$ T cells from similar cultures, or IL-2-cultured PBL all remained virtually unchanged in the level and distribution of mAb C1.7 staining.

EXAMPLE 4

Detection of p38 in NK Cell Lysates by Western Blotting

Purified, cultured NK cells were lysed with 1% NP-40, 5 mM PMSF, and 10 µg/ml leupeptin in PBS. The lysate equivalent of $2\times10^8$ cells was loaded onto 5–20% continuous gradient polyacrylamide slab gels (1.0 mm thickness) and SDS-PAGE was performed as described by U. K. Laemmli, *Nature (Lond)*, 227:680 (1970) under nonreducing and reducing (2% β-mercaptoethanol) conditions. After electrophoresis, resolved proteins were transferred to nitrocellulose using a semi-dry transblotter (Bio-Rad Laboratories, Richmond, Calif.). The blots were cut into strips and probed with various mAbs specific for NK cell proteins: C1.7 and TIA-2 (anti-CD3ζ). These mAbs were detected by $^{125}$I-labeled, affinity-purified GαMIg. The strips were reassembled and subjected to autoradiography.

A representative blot from one donor indicated that mAb C1.7 detected a single immunoreactive species of 38 kD (p38) under both nonreducing and reducing conditions. The anti-CD3ζ (TIA-2) control detected a 34-kD protein under nonreducing conditions which reduced to a single 17-kD immunoreactive species.

EXAMPLE 5

Effect of mAb C1.7 on NK Cell Cytotoxic Activity

To demonstrate mAb C1.7-induced, NK cell-mediated cytotoxicity, a variety of chromium release cell cytotoxicity assays were performed. mAb C1.7 was able to activate NK cell cytotoxicity in different assay systems.

A. Antibody-Redirected Lysis Assay

In antibody-redirected lysis assays, purified, cultured NK cells or PBL were used as effectors in standard 3 hour incubation $^{51}$Cr release assays, performed in U-bottomed microliter plates (Costar Corp., Cambridge, Mass.) using $^{51}$Cr-labeled $Fc\gamma R^+$ P815X2 target cells ($10^4$ cells/well). The effector and target cells were in the presence of medium alone or medium with 0.1 µg/ml of mAb B159.5 (anti-CD56), mAb 3G8 (anti-CD16), or mAb C1.7 at E:T ratios of 2.5:1, 5:1, 10:1, and 20:1 for the NK cell effectors and E:T ratios of 6:1, 12:1, 24:1 and 48:1 for the PBL effectors. All assays were performed in triplicate.

Results were quantitated by calculating the percentage of specific $^{51}$Cr release and in some assays the number of lytic units per $10^7$ cells at 45% specific lysis were calculated using the linear regression to a modified Van Krogh's equation [G. Trinchieri et al, *Transplant. Proc.*, 5:1631 (1973)].

The results demonstrated that soluble mAb C1.7 was capable of substantially increasing both cultured and fresh NK cell-mediated antibody-redirected lysis against the FcγR⁺ P815X2 target cells. In all donors the levels of specific $^{51}$Cr release observed with mAb C1.7 were comparable to those observed with anti-CD16 (3G8) treatment and markedly greater than those observed with anti-CD56 (B159.5) treatment or medium alone. Both mAb C1.7- and anti-CD16 (3G8)-induced redirected lysis result in apoptotic events in P815X2 target cells as measured by decreased propidium iodide staining and fragmentation of target cell DNA.

B. Hybridoma-Redirected Lysis Assay

In the hybridoma-redirected lysis assays, purified, cultured NK cells were used as effectors against the $^{51}$Cr-labeled targets: myeloma fusion partner, PX63.Ag8.653, or the hybridomas 3G8, B159.5, or C1.7. Results were quantitated as described in Part A of this example.

The results indicated that the C1.7 hybridoma was sensitive to NK cell cytotoxicity, although in most experiments, to a lesser extent than the anti-CD16 hybridoma (3G8). In these experiments, neither the anti-CD56 hybridoma (B159.5) nor the PX63.Ag8.653 myeloma fusion partner were significantly lysed by the NK cells. The decreased efficiency of the C1.7 hybridoma in inducing cytotoxicity compared with the 3G8 hybridoma could be due to the fact that the surface Ig expression of the C1.7 hybridoma was much lower than that observed for the 3G8 hybridoma.

EXAMPLE 6

Effect of mAb C1.7 Stimulation on BLT-Esterase Release from NK Cells

The ability of mAb C1.7 to induce the release of the granule enzyme BLT-esterase from cultured NK cells was determined using a variety of stimulation protocols.

N-Carbobenzoxy-L-thiobenzyl ester (BLT) esterase activity in cell-free supernatants was determined in a microtiter assay. Purified, cultured NK cells were incubated for 3 hours with FcγR⁺ P815X2 target cells at a ratio of 10:1 in the presence of medium alone or medium supplemented with 0.1 µg/ml of mAb B159.5, mAb C1.7, or mAb 3G8. After incubation, 50 µl of cell-free supernatant fluid was added to 100 µl of 0.1 mg/ml dithiobis-2-nitrobenzoic acid and 0.1 mg/ml Nα-carbobenzoxy-L-Lys-thiobenzyl ester (Sigma Chemical Co.) in 0.1M Tris and 1 mM MgCl₂, pH 7.5. BLT-esterase activity was determined by increased absorbance at 405 nm. Total BLT-esterase activity was determined from lysed (freeze/thaw three times), untreated NK cells. The percentage of specific BLT-esterase release was calculated as experimental BLT-esterase activity—spontaneous (untreated) BLT-esterase activity/total BLT-esterase activity×100.

NK cell effectors from the same donors used in the BLT assays were also assayed in parallel for antibody-redirected cytotoxicity of $^{51}$Cr-labeled P815X2 cells as described.

The summarized results of four such experiments, were reported as mean percentage of specific release plus or minus the standard error (n=4). The percent specific release of $^{51}$Cr for medium alone was about 8%, for B159.5 was about 9%, for C1.7 was about 63%, and for 3G8 was about 58%. The percent specific release of BLT esterase for medium alone was about 15%, for B159.5 was about 17%, for C1.7 was about 16%, and for 3G8 was about 78%. Clearly, both mAb C1.7 and mAb 3G8 induced cytotoxic activity in the NK cells when compared with the anti-CD56 (B159.5) and medium controls. However, only mAb 3G8 was capable of stimulating BLT-esterase release with no increase observed in C1.7-treated cultures.

In addition to having mAb C1.7 presented to NK cells by the FcγR⁺ target cell P815X2 as described above, alternatively, mAb C1.7 was immobilized on a plastic support, bound to Sepharose 4B, or absorbed to plastic-bound GαMIg. Under no conditions were detectable levels of BLT-esterase release observed above controls after mAb C1.7 stimulation. By contrast, anti-CD16 stimulation resulted in substantial increases in BLT-esterase levels with all four stimulation methods.

EXAMPLE 7

Stimulation of NK Cell Lymphokine Production by mAb C1.7

Using the same stimulation protocols used to induce BLT-esterase release, the effect of mAb C1.7 on NK cell lymphokine production was examined.

Purified, cultured NK cells were incubated with P815X2 cells at an effector to target (E/T) ratio of 10:1 in U-bottomed microtiter plates for 18 hours in the presence or absence of mAb C1.7 (0.1 µg/ml). Stimulation was performed in medium alone or in medium supplemented with rIL-2 (100 U/ml) or rNKSF/IL-12 (1 ng/ml). After 18 hours, cell-free supernatants were collected and the concentrations of IFN-γ and IL-8 were determined in the cell-free supernatant fluids.

IFN-γ was measured by RIA as described by M. C. Cuturi et al, *J. Exp. Med.*, 165:1581 (1987) using mAbs B133.1 and B133.5. IL-8 was measured by ELISA using mAb Mc.a-NAP-1 and the alkaline phosphatase-conjugated goat polyclonal antibody Pc.a-NAP-1. Specifically, the ability of mAb C1.7 to induce the production of IFN-γ, IL-8, and TNF-α was determined by RIA and ELISA assays.

The results of these assays are reported in Table 1 below. Significance was determined by Student's t test for dependent samples.

TABLE 1

| mAb C1.7-induced Lymphokine Production | | | |
|---|---|---|---|
| Treatment* | mAb C1.7 | IFN-γ, mean U/ml + SE (n = 10) | IL-8, mean pg/ml + SE (n = 6) |
| Medium | − | 5.2 ± 2.1 | 150.5 ± 50.8 |
| Medium | + | 5.5 ± 1.1 | 236.4 ± 81.3‡ |
| rIL-2 | − | 61.3 ± 8.2 | 251.2 ± 75.2 |
| rIL-2 | + | 208.7 ± 25.5§ | 550.9 ± 135.0§ |
| rNKSF/IL-12 | − | 60.6 ± 12.2 | 243.4 ± 100.5 |
| rNKSF/IL-12 | + | 247.8 ± 30.9§ | 496.9 ± 161.7‡ |

‡P < 0.05.
§P < 0.005.

The C1.7 antibody was capable of inducing significant increases in IFN-γ and IL-8 production from cultured NK cells only when soluble mAb C1.7 (0.1 µg/ml) was presented to the NK cells by FcγR⁺ P815X2 cells. It is possible that mAb C1.7-induced lymphokine production requires accessory molecular interactions between other receptor-ligand pairs on the NK cells and presenting target cells which were not available when mAb C1.7 was presented on inert supports such as plastic surfaces or Sepharose beads. In addition, the fluidity of the presenting cell membrane in comparison to the rigidity of a solid support might also contribute to more efficient stimulation.

As shown in Table 1, increases in IFN-γ production were observed in the presence of rIL-2 (100 U/ml) or rNKSF/IL- 12(1 ng/ml), whereas increases in IL-8 production occurred with mAb C1.7 alone or in the presence of rIL-2 or NKSF/IL-12.

Under all stimulation conditions mAb C1.7 treatment had no effect on TNF-α production. Unlike mAb C1.7, anti-CD16 (3G8) treatment induced comparable lymphokine (IFN-γ and IL-8) production under all four stimulation protocols and anti-CD56 (B159.5) treatment had no effect on IFN-γ and IL-8 production under any of the conditions tested.

EXAMPLE 8

Effect of mAb C1.7 Treatment on Lymphocyte Proliferation

The abilities of both soluble and plastic-bound mAb C1.7 to affect [$^3$H]TdR uptake of fresh PBL or purified, cultured NK cells alone or in the presence of increasing doses of rNKSF/IL-12 or rIL-2 was measured.

Fresh PBL or purified, cultured (7 day) NK cells were cultured in flat-bottomed Linbro/Titertrek plates (Flow Laboratories, Inc.) at $10^5$ cells/well for 6 or 3 days, respectively. PBL were cultured in the presence of recombinant natural killer cell stimulatory factor/IL-12 (rNKSF/IL-12) (0.1 ng/ml) alone or with 10, 100, or 1,000 U/ml of rIL-2 in medium alone or medium with 1 µg/ml of soluble mAb C1.7 or anti-CD3 antibody (OKT3).

NK cells were cultured in medium alone or medium supplemented with 10, 100, or 1,000 U/ml of rIL-2 in wells that were treated with 0.1M bicarbonate buffer, pH 9.5, alone or bicarbonate buffer in the presence of no antibody or 5 µg/ml of the following antibodies bound to plastic: mAb C1.7, mAb 3G8, or mAb B159.5. Before cells were added, the bicarbonate buffer was removed and the wells were washed twice with PBS to remove unabsorbed antibodies. Thymidine [methyl-$^3$H] ([$^3$H]TdR; New England Nuclear, Boston, Mass.) was added (1 µCi/well) during the last 6 hours of culture. Cells from triplicate cultures were harvested on glass fiber filters and [$^3$H]TdR incorporation was determined by liquid scintillography.

In all experiments, NK cells incorporated far lower amounts of thymidine [methyl-$^3$H] ([$^3$H-TdR]) than PBL. Soluble C1.7 induced a two- to four-fold enhancement of PBL [$^3$H]TdR incorporation in PBL cultured for 6 days in the presence of 0.1 ng/ml of rNKSF/IL-12 and increasing doses (10–1,000 U/ml) of rIL-2. This enhancement was greater than that observed with soluble anti-CD3(OKT3) treatment, but OKT3 treatment resulted in enhanced [$^3$H]TdR uptake in the absence of either cytokine. Treatment of PBL with plastic-bound mAb C1.7 consistently resulted in moderately decreased [$^3$H]TdR uptake by the cells.

When purified, cultured (7 days) NK cells were treated in a similar fashion for 3 days, the effect of mAb C1.7 (soluble or plastic bound) was antagonistic to the effects of increasing doses of rIL-2 or rNKSF/IL-12. In all experiments, anti-CD56 (B159.5) treatment had no effect on proliferation when compared with medium controls, and anti-CD16 (3G8) treatment, similar to what was observed in cultures treated with mAb C1.7, was antiproliferative.

EXAMPLE 9

Signal Transduction through p38 on NK Cells

The abilities of mAb C1.7 stimulation to initiate polyphosphoinositol turnover and increases in [Ca$^{2+}$]$_i$ in purified, cultured NK cells were measured.

A. Phosphoinositide Turnover

Determination of intracellular accumulation of inositol phosphates (IP) was performed as described [M. A. Cassatella et al, *J. Exp. Med.*, 169:549 (1989)]. Briefly, purified NK cells (5–10×10$^6$/ml) were incubated in inositol-free RPMI-1640 medium (Flow Laboratories, Inc.) with 5% FBS for 18 hours at 37° C. in the presence of myo-[$^3$H]inositol (10 µCi/ml; Amersham Corp., Arlington Heights, Ill.). After incubation, cells were resuspended in HBSS (1 mM CaCl$_2$, 5.6 mM glucose, 20 nM Hepes, and 10 mM LiCl, pH 7.4) (GIBCO BRL, Gaithersburg, Md.). C1.7 F(ab')$_2$ fragments (1 µg/ml) and goat anti-mouse immunoglobulin (GαMIg) F(ab')$_2$ (20 µg/ml) fragments were added at about 30 seconds and 4 minutes, respectively, of a 7 minute span to duplicate samples of 10×10$^6$ cells.

IP$_1$, IP$_2$, IP$_3$, and IP$_4$ were extracted from the cells (10×10$^6$/ duplicate samples) at different times after addition of mAb C1.7 F(ab')$_2$ with or without F(ab')$_2$. The different IPs (IP$_1$–IP$_4$) were measured as cell-incorporated counts per minute after anion exchange chromatography of each sample on a 1-ml Agl-X8 column (Bio-Rad Laboratories). Columns were washed with a four-step discontinuous gradient of 0.1M formic acid containing 0.2, 0.5, 0.8, and 1.0M ammonium formate to elute IP$_1$, IP$_2$, IP$_3$, and IP$_4$, respectively. Radioactivity of each fraction was measured by liquid scintillation counting in a β counter. IP, IP$_2$, IP$_3$, and IP$_4$ basal cpm values were 405, 119, 79, and 55, respectively.

The results indicated that within 15–30 seconds after crosslinking with GαMIg F(ab')$_2$ (20 µg/ml) the C1.7 F(ab')$_2$ (1.0 µg/ml) induced substantial increases in the second messenger, inositol triphosphate (IP$_3$), followed by induction of inositol bisphosphate (IP$_2$) and inositol tetrakiphosphate (IP$_4$).

B. [Ca$^{2+}$]$_i$ Measurement

[Ca$^+$]$_i$ increases in NK cells were determined as previously described in Cassatella et al, cited above. Briefly, purified NK cells were labeled with the fluorescent Ca$^{2+}$ indicator fura-2/AM (2 µM) (Calbiochem-Novabiochem Corp.). After fura-2 loading, cells were washed and resuspended in HBSS and fluorescence measurements were performed in a spectrofluorometer (Perkin Elmer Corp., Norwalk, Conn.) equipped with a thermostatic cuvette holder maintained at 37° C. with continuous stirring. Each sample contained 5×10$^6$ cells in 1.7 ml of HBSS. The C1.7 F(ab')$_2$ reagent (0.5 µg/ml final) and the GαMIg F(ab')$_2$ reagent (10 µg/ml final) were added at about 30 seconds and about 2 minutes into the 7 minute period, respectively, and changes in fluorescence were recorded as a function of time. [Ca$^{2+}$]$_i$ was calculated as previously described in Cassatella et al, cited above.

Similar to the induction of polyphosphoinositol turnover, the F(ab')$_2$ of mAb C1.7 (0.5 µg/ml) induced increases in [Ca$^{2+}$] after crosslinking with the GαMIg F(ab')$_2$ (10 µg/ml) reagent.

In all donors anti-CD16 (3G8) stimulation resulted in low level generation of IPs and [Ca$^{2+}$]; increases when the antibody was used alone and these levels were greatly increased upon crosslinking, consistent with previously published results [Cassatella et al, cited above]. Treatment of NK cells with the anti-CD56 antibody, B159.5, had no effect on either of these signal transduction events with or without the addition of GαMIg.

EXAMPLE 10

Ability of p38$^+$ CD8$^+$ T Cells to Mediate Non-MHC-restricted Cytotoxicity

Upon culture (3–6 days) with lymphokines such as IL-2 or NKSF/IL-12, cytotoxic T cells acquire the ability to lyse target cells in a non-MHC-restricted manner. Because p38 is expressed by ~50% of fresh CD8$^+$ T cells, an experiment was conducted to determine whether p38$^+$ and p38$^-$ CD8$^+$ T cells, obtained from PBL cultured for 5 days in the presence of rIL-2, differed in their ability to mediate non-MHC-restricted cytotoxicity.

PBL were isolated from healthy donors, depleted of NK cells and monocytes by antiglobulin rosetting with mAb anti-CD16 (B73.1, 3G8), anti-CD56 (B159.5), and anti-CD14 (B52.1), and cultured for 5 days with 200 U/ml rIL-2. After culture, all of the NK-depleted (NK$^-$) PBL were subjected to antiglobulin rosetting with anti-CD4 (B66.6) and the anti-CD16, anti-CD56, and anti-CD14 reagents, with half of the cells also being rosetted with mAb C1.7.

A two-color immunofluorescence analysis was performed with the above-indicated antibodies on rIL-2-cultured (5 days), NK-depleted lymphocytes from a representative donor FIG. 1A(i), 1A(ii), 1A(iii), and 1A(iv). Notably, there were no detectable CD16$^+$ cells in the cultured PBL (panel 1) and the percentage of C1.7+/CD8$^+$ T cells was consistent with that observed in fresh PBL (panel 4). The small population (~4%) of p38$^+$/CD3$^-$ cells (panel 2) present in this donor and some others, did not appear to affect the level of non-MHC-restricted cytotoxicity, because sorted (FACS®) CD3$^+$ cells and total unsorted populations exhibited the same degree of non-MHC-restricted cytotoxic activity.

Cultured lymphocytes were depleted of CD4$^+$ cells or both CD4$^+$ and p38$^+$ cells as described above and used as effectors in 3-hour chromium release assays against $^{51}$Cr-labeled Daudi target cells at the E:T ratios: 6:1, 12:1, 24:1 and 48:1. The results from 51Cr release assays using CD8$^+$ T cells from four separate donors were reported in FIG. 1B as the mean percentage of specific $^{51}$Cr releast±SE (n=4). The data demonstrates that the overwhelming majority of the non-MHC-restricted cytotoxic activity of the rIL-2-cultured CD8$^+$ T cells is contained within the p38$^+$ subset. Experiments using K562, THP-1, Jurkatt, U937, and P815X2 target cells yielded similar results. The different non-MHC-restricted cytotoxic activity between p38$^+$ and p38$^-$ CD8$^+$ rIL-2-cultured T cells was not restricted to tumor-derived targets, since virally infected (varicella zoster virus, herpes simplex virus, and cytomegalovirus) FS4 target cells were also lysed with much greater efficiency by p38$^+$ than by p38$^-$ effectors.

EXAMPLE 11

Effect of F(ab')$_2$ Fragments of mAb C1.7 on Non-MHC-restricted Cytotoxicity

This experiment was conducted to assess the ability of F(ab')$_2$ fragments of mAb C1.7 to alter non-MHC-restricted cytotoxicity, specifically, to inhibit spontaneous cytotoxicity. Non-MHC-restricted cytotoxicity assays were performed with either $^{51}$Cr-labeled Daudi or K562 target cells.

Various populations of lymphocytes, i.e., PBL or rIL-2-cultured (5 day) NK-depleted lymphocytes, were used as effectors against $^{51}$Cr-labeled Daudi and K562 target cells in 3 hour chromium release assays. Assays were performed in the presence of mAb C1.7 F(ab')$_2$ (○) or mAb 3G8 F(ab')$_2$ (●) at the concentrations: 1, 10, 20, 30, 40, or 50 µg/ml.

Figure 2B:
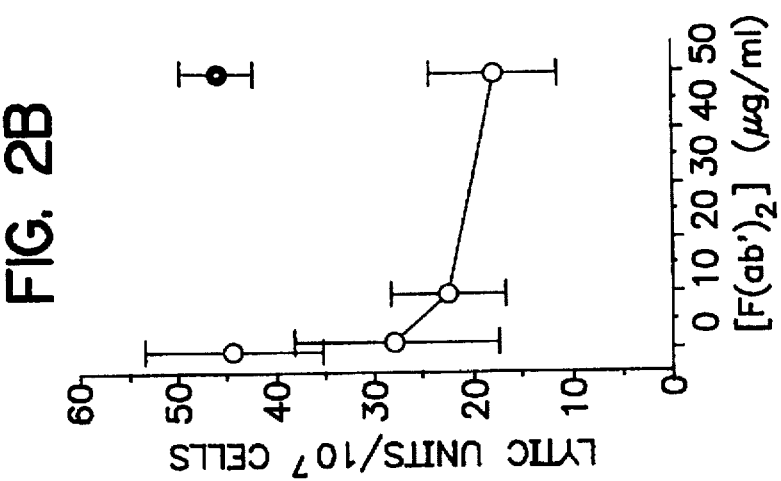
FIG. 2B is a graph demonstrating the results of a similar assay in which IL-2-cultured (5 day), NK-depleted lymphocytes were used as effectors against the same target cells. Symbols and results are as reported in FIG. 2A.
Figure 2A:
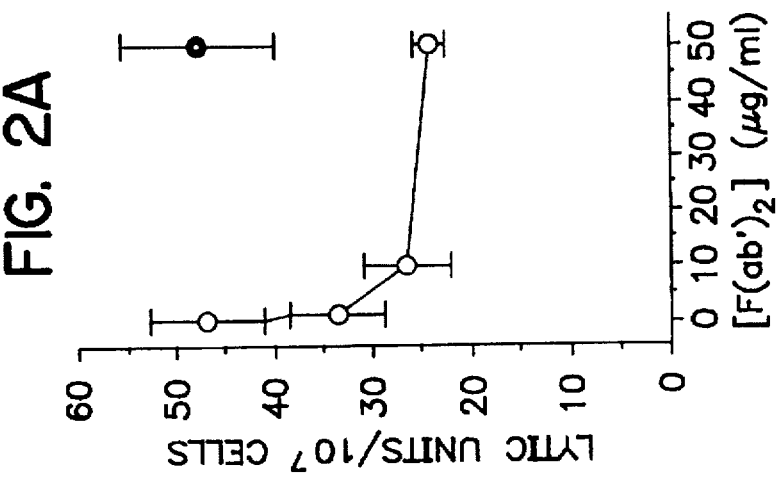
FIG. 2A is a graph measuring the inhibition of spontaneous cytotoxicity by mAb C1.7 F(ab')$_2$ using PBL as effectors in 3 hour chromium release assays against $^{51}$Cr-labeled K562 target cells. Assays were performed in the presence of mAb C1.7 F(ab')$_2$ (○) or mAb 3G8 F(ab')$_2$ (●) as described in Example 11. Results are presented as mean lytic units/10$^7$ cells±SE (n=3).

As shown in FIGS. 2A through 2C, results are presented as mean lytic units/10$^7$ cells+SE (n=3). 10 and 50 µg/ml of F(ab')$_2$ fragments of mAb C1.7 reduced non-MHC-restricted cytotoxicity of fresh PBL against K562 (FIG. 2A) target cells and of NK-depleted rIL-2 (5 days) cultured PBL against K562 (FIG. 2B) and Daudi target cells (FIG. 2C). This inhibition appears specific because 50 µg/ml of anti-CD16 (3G8) F(ab')$_2$ had no effect on the lytic ability of the lymphocytes. In five out of five donors, C1.7 F(ab')$_2$ had no effect on the cytotoxic activity of purified, cultured NK cells against Daudi and K562 target cells.

EXAMPLE 12

Isolating p38 by Screening of a NK Cell Library

The following procedure provides a means for isolating and identifying the p38 receptor in more detail.

A. Transfection

About 5×10$^5$ COS-7 cells [ATCC CRL 1651] are plated in each of 24 60 mm plates, in 3 ml of RPMI medium and 5% FCS. Cells are incubated overnight at 37° C. Aliquots of a human NK cell plasmid library (3 µg/plate) diluted in 100 µl of Opti-MEM/plate, and aliquots of lipofectin (10 µl/plate) diluted in 100 µl of Opti-MEM (Gibco; BRL)/plate are prepared. These aliquots are mixed and incubated for 10–15 minutes at room temperature. Meanwhile the plates are washed with 3 ml/plate of Opti-MEM to eliminate serum. Each 200 µl aliquot of DNA/lipofectin is added to 800 µl of Opti-MEM. The plates are drained, mixed and the 1 ml mixture is added to each plate.

Plates are incubated 6–24 hours at 37° C. 2 ml of complete medium is added per plate, and plates are incubated for a total of 48–72 hours.

B. Preparation of Antibody-plates

Anti-mouse-Ig antibody (e.g., Cat. No. 1097 105, Boehringer) are added to 2.5 µg/ml in 50 mM Tris (pH 9.5), and 10 ml of the solution is added immediately to 100 mm polystyrene bacteriological plates. These plates are incubated 40 hours at room temperature. The buffer is decanted and plates are washed four times with PBS, then blocked overnight at +4° C. in PBS+ 1 mg/ml BSA+ 0.02% Na Azide. The solution is poured off and the plates stored wrapped at ~20° C.

C. Panning

The transfected cells are detached by incubation in PBS+ 1 mM EDTA+ 0.02% Na Azide at 37° C. for 30 hours. They are pooled and centrifuged, then resuspended in 5 ml of cold PBS+ 10 mM EDTA+ 5% FBS+ monoclonal antibody C1.7 at the correct dilution (e.g., ~0.1 µg/ml). Cells are incubated for 1 hour on ice.

Dilute 1: One plate is diluted with PBS+ 1 mM EDTA+ 0.02% Na Azide and layered on 10 ml of PBS+ 1 mM EDTA+ 0.02% Na Azide containing 2% Ficoll 400. This plate is spun at 400 g for 5 hours. The supernatant is carefully aspirated and the pellet is resuspended in 3.6 ml of PBS+ 10 mM EDTA+ 5% FBS. 300 µl is added to each panning plate containing 3 ml of PBS+ 10 mM EDTA+ 5% FBS.

The plate is incubated 2 hours at room temperature, and washed gently three times with PBS+ 10 mM EDTA+ 5% FBS, followed by draining. 400 µl of 10 mM EDTA/0.6% SDS is added in each plate and distributed. These plates are incubated 5 hours at room temperature, then the lysate is collected into centrifuge tubes.

D. DNA extraction and transformation

To the lysate is added 5M NaCl to a final concentration of 1M. The tube is incubated at least 8 hours at +4° C. The tube is spun for 30 hours at +4° C. at 17,000 g. The supernatant is collected and extracted with phenol/chloroform extract, then is extracted with chloroform. The supernatant is Centricon purified and washed with TE, centrifuged at 3000 rpm for 3 minutes.

After collection, half of the supernatant is used for transformation of 2×100 µl of super-competent E. coli MC1061/

P3 cells [InVitrogen Corp., Catalog No. C663-030]. The transfected cells are plated on two large LB+Amp/Tet plates and are incubated 24–48 hours at 37° C.

Minipreps are made from 18 colonies, and a large prep from all colonies. The minipreps are analyzed, and the larger prep DNA used for the second cycle of transfections.

Following the second transfection, the mAb C1.7 is used to identify the cells which are expressing the p38 receptor. The plasmids containing the p38 cDNA are isolated from bacterial clones. To assure that the plasmid truly expresses a protein that reacts with C1.7, COS cells are transfected with individual plasmids putatively expressing the p38 cDNA.

Upon identification of such a plasmid, the cDNA insert will be subcloned and sequenced by conventional techniques. See, for example, A. Aruffo and B. Seed, *Proc. Natl. Acad. Sci. USA*, 84(23):8573–7 (1987). Briefly, positive clones can be rescreened to homogeneity at low density and compared with one another by restriction mapping and Southern blot analysis to identify identical or overlapping clones. The sequencing data from the identified clones can be used to provide further support and means for identification of the genes for either the receptor or the entire antigen in which it is present, and aid in the identification of related molecules. Other methods for obtaining the sequence of the p38 receptor are known and available to one of skill in the art.

EXAMPLE 13

Lymophocyte Distribution of p38

A. Because approximately 30% of human NK cells express the CD8 surface antigen [B. Perussia et al, *J. Immunol.*, 131:223–231 (1983)], three color immunofluorescense was performed to distinguish p38 expression on the lymphocyte subsets (i.e., between the CD8$^+$/p38$^+$ NK cell and the CD8$^{+/P}$38$^+$ T cell populations in peripheral blood from a variety of donors.

PBL from a representative donor were stained simultaneously with anti-CD16 (mAb B73.1), anti-CD8 (mAb B116.1) and mAb C1.7 monoclonal antibodies and analyzed by flow cytometry. When total (ungated) lymphocytes were analyzed for p38 and CD8 expression, three populations of p38$^+$ cells were detected: p38+/CD8$^-$; p38$^+$/CD8$^{dim}$ and p38$^+$/CD8$^{bright}$.

By gating on the CD16$^-$ and CD16$^+$ populations separately, it was conclusively demonstrated that the p38$^+$/CD8$^{bright}$ population corresponds to the CD8$^+$/CD16$^-$ T cell subset, whereas, the p38+/CD8$^-$ and p38$^+$/CD8$^{dim}$ populations correspond to the CD16$^+$ NK cell subset.

On average 100% of CD16$^+$ NK cells and 48.1±8.5% (mean±SE; n=5) of CD8$^+$ T cells were shown to express the p38 surface molecule in these experiments.

Activated NK cells from 8 day culture with certain EBV-transformed B cell lines, activated $\gamma/\delta^+$ T cells from similar cultures, and IL-2 cultured PBL all remained virtually unchanged in the level and distribution of mAb C1.7 reactivity.

B. Two populations of CD8$^+$ T cells are present in peripheral blood based on the expression of p38. To determine whether the p38$^+$ and p38$^-$ phenotypes of these T cells were stable or modulated by activation or culture conditions, fluorescence activated cell sorting (FACS) was used to obtain highly enriched preparations of either CD8$^+$/p38$^+$ or CD8$^+$/p38$^-$ T cells for long term culture and cloning. The two populations obtained were cultured in bulk (0.5 µg/ml PHA, 40 U/ml rIL-2 in RPMI-1640 medium [Flow Laboratories, McClean, VA] with 10% human AB serum) for one week and then cloned by limiting dilution. After one week the phenotype of the p38$^+$ and p38$^-$ bulk populations remained virtually unchanged. Moreover, the p38$^+$ and p38$^-$ clones obtained from these cultures also maintained a stable phenotype for >1 month. Based on these results, the p38 phenotypic distinction of lymphocyte subsets is stable and independent of cell activation.

C. Similarly, three color immunofluorescence has been used to compare surface distribution of p38 and two other cell surface markers, S6F1 (anti-LFA-1 epitope) and CD29, which have been used to distinguish between CD8$^+$ T cell populations with high and low cytotoxic potential.

Although these two latter surface markers are expressed by all lymphocytes, there are distinct bright and dim populations detectable by immunofluorescence. Morimoto et al, *Nature*, 330:479–482 (1987) and Sohen et al, *Cell. Immunol.*, 128:314–328 (1990) demonstrated that the S6F1$^{bright}$ and CD29$^{bright}$ CD8$^+$ T cells exhibit significantly higher cytotoxic activity than S6F1$^{dim}$ and CD29$^{dim}$ CD8$^+$ T cells.

Using three color immunofluorescence analysis (S6F1 or CD29 vs. CD8 vs. C1.7), the p38$^+$ CD8$^+$ T cells are all found within the S6F1$^{bright}$ and CD29$^{bright}$ subset, whereas, the p38$^-$ CD8$^+$ T cells are all S6F1$^{dim}$ and CD29$^{bright}$. Recent data has shown that upon $_{in\ vivo}$ activation of cells, 100% of activated CD8 cells are S6F$^+$ and CD29$^+$, and many p38$^-$ cells became p38$^+$. However, there remains a sizeable minority of highly activated p38$^-$ CD8$^+$ cells. These latter cells are the low cytotoxicity, high IL-4 producing cells.

D. CD28 is another CD8$^+$ T cell antigen which has been used in attempts to distinguish between subsets of these T cells. [M. Azuma et al, *J. Immunol.*, 50:1147 (February 1993)]. However, CD28 denotes a slightly different population of cells than does p38. For example, comparative data has indicated that the low cytotoxic p38$^-$ CD8$^+$ positive cells are CD28$^+$. Conversely, the highly cytotoxic p38$^+$ CD8$^+$ cells are CD28$^-$. However, CD28 is also found on CD4 cells which do not express the p38 protein.

No other antigen markers have been described with this precise distribution of p38.

EXAMPLE 14

Bifunctional Antibodies

Hybrid antibodies can be prepared from mAb C1.7. Such hybrid antibodies include bifunctional antibodies, chimeric antibodies, quadromas and the like. These antibodies may be prepared from the mAb C1.7 employing a variety of conventional means.

For example, the complete IgG of C1.7, its F(ab')$_2$ or Fab fragment is chemically cross-linked [see, A. Lanzaveccia, cited above; and T. Nitta et al, *Eur. J. Immunol.*, 19:1431 (1989)] to another antibody, e.g., an anti-tumor or viral antigen. Alternatively, a bispecific antibody is obtained by in vitro disulfide exchange from IgG that have been reduced, denatured in acid, and reassembled under oxidizing conditions as described in J. Petersen et al, *J. Biol. Chem.*, 249:5633 (1974). If no preferentially reassociation of homologous heavy and light chains is observed, one molecule out of 10 is expected to have the desired specificity, and purification steps are performed [see, e.g., M. R. Suresh et al, *Meth. Enzymol.*, 121:210 (1986)].

Still another method of preparing hybrid antibodies involves the production of a quadroma. According to this method, the C1.7-producing hybridoma and the hybridoma of a selected target cell antibody are fused together and selected under appropriate experimental conditions, in order to obtain hybrid-hybridomas producing the four chains. See, e.g., Suresh et al, cited above. If random association is observed, one antibody out of 10 produced by the quadroma has the correct dual specificity.

To select the quadromas against the two parental cell lines, several methods may be employed. The two parental hybridomas are poisoned with two distinct irreversible site specific inhibitors before fusion (e.g., emetine and actinomycin D) that allow functional recombination in the hybrid cells. Alteratively, the C1.7 line is made HGRPT deficient by selection in 8-azaguanine and fused with another hybridoma treated with an irreversible inhibitor, the hybrids thereafter being selected in HAT medium. The HGRPT deficient cell line may be fused with another hybridoma made thymidine-kinase deficient by selection in BUDR as described in J. T. Wong et al, *J. Immunol.*, 139:1369 (1987). Hybrids are selected in HAT medium.

Still another method involves making the HGRT deficient cell line G-418-resistant by infection with a retroviral vector carrying the neomycin resistance gene. This C1.7 line is fused with any other hybridoma and the hybrids selected in HAT medium and G-418. This latter alternative is preferred because allows the production of a quadroma between C1.7 and another other selected hybridoma.

Another method useful for making bifunctional and chimeric antibodies are known to those of skill in the art. See, e.g., International Patent Application WO92/10209, published Jun. 25, 1992. See, also, the methods described in Milstein and Cuello, *Nature*, 305:537–540 (1983); Staerz et al, *Nature:* 314:628–631 (1985); Perez et al, *Nature:* 316:354–356 (1985); Clark and Waldmann, *JNCI,* 79:1393–1401 (1987); Gilliland et al, *Proc. Natl. Acad. Sci. USA,* 85:7719–7723 (1988); Staerz et al, *Eur. J. Immunol.,* 17:571–574 (1987); DeMonte et al, *Proc. Natl. Acad. Sci., USA,* 87:2941–2945 (1990); Lenz and Weidle, *Gene:* 87:213–218 (1990)].

Bifunctional antibodies can also be produced by reduction of monoclonal antibodies to the single heavy chain associated with its single light chain (HL form), mixing with a second monoclonal antibody followed by reoxidation to produce mixed antibodies [Staerz and Bevan, *Proc. Natl. Acad. Sci. USA,* 83:1453–1457 (1986)].

Other techniques include recombinant genetic engineering techniques known to those of skill in the art. See, e.g., Sambrook et al, "Molecular Cloning. A Laboratory Manual." 2nd edition, Cold Spring Harbor Laboratory, Cold Spring Harbor, N.Y. (1989). Conventional chemical synthesis methods may also be used in addition to genetic engineering methods in some instances.

Bifunctional antibody fragments, both Fab domain fragments and heavy chain replacement fragments, are constructed and expressed by essentially following the methods of W. D. Huse et al, *Science,* 246:1275–1281 (1898), which is incorporated by reference herein for further descriptions of methods and materials known to those of skill in the art.

The hybrid or bifunctional antibodies can be tested in vitro for their ability to induce killing of antigen positive target cells using different types of effector cells and in vivo for the ability of adaptively transferred human lymphocytes to prevent growth of human tumors in nude or scid mice.

In additional to bifunctional antibodies between C1.7 and tumor associated antigens or virus antigens, antibodies against other pathogens may be prepared for use against, for example, parasites sensitive to the cytotoxic effector of T or NK cells. Antibodies against activation markers on lymphocytes are useful for immunosuppression in transplantation or in autoimmune diseases. Such other targets include antibodies against the p55 chain of the IL-2 receptor.

In additional to bifunctional antibodies C1.7 may be cross linked to other receptors or ligands, the counterpart of which is expressed on the cells to be eliminated. For example, antibody C1.7 may be cross-linked to CD4, that would bind to gp120 on the surface of HIV infected cells and would induce their killing by C1.7 effector cells.

The hybrid or bifunctional antibodies produced according to present invention may be used as a diagnostic agent to detect qualitatively or quantitatively the presence of a selected target antigen in a biological sample. The bifunctional antibody for such use may be provided with one or more detectable labels. The first antigen binding site and the second antigen binding site of the antibody may each bear a detectable label. The label may be one which is capable of visual detection or may be selected from systems detectable by other means, including, for example, fluorescent compounds, radioactive compounds or elements or immunoelectrodes. These and other appropriate label systems are known to those of skill in the art.

Additionally, the bifunctional antibody produced by the method of this invention may be used in therapeutic regimens, such as the treatment of cancers. For example, a bifunctional antibody having a binding site for a tumor cell surface antigen and for a T-cell surface receptor would be administered, by in vivo or ex vivo therapy, so that lysis of the tumor cells by T cells is enhanced. Similar therapeutic or diagnostic functions are designed depending on the selection of other biological targets susceptible to lysis by $CD8^+$ T cells or NK cells.

Numerous modifications and variations of the present invention are included in the above-identified specification and are expected to be obvious to one of skill in the art. Such modifications and alterations to the compositions and processes of the present invention are believed to be encompassed in the scope of the claims appended hereto.

What is claimed is:

1. A monoclonal antibody which specifically binds to the same epitope as the C1.7 monoclonal antibody, said C1.7 monoclonal antibody being produced by the hybridoma cell line deposited as ATCC HB 11717.

2. A hybridoma cell line secreting mAb C1.7 and having ATCC accession no. HB-11717.

3. The monoclonal antibody produced by the hybridoma cell line C1.7, said cell line being deposited as ATCC HB 11717.

* * * * *